United States Patent [19]
Steer

[11] Patent Number: 5,843,053
[45] Date of Patent: Dec. 1, 1998

[54] OSTOMY COUPLING

[75] Inventor: Peter L. Steer, Sussex, England

[73] Assignee: Bristol-Myers Squibb Company, New York, N.Y.

[21] Appl. No.: 725,868

[22] Filed: Oct. 4, 1996

[30] Foreign Application Priority Data

Aug. 20, 1996 [GB] United Kingdom .................. 96 17410

[51] Int. Cl.⁶ ...................................................... A61F 5/44
[52] U.S. Cl. .......................................... 604/342; 604/338
[58] Field of Search ................................... 604/332, 338, 604/342

[56] References Cited

U.S. PATENT DOCUMENTS

| | | | |
|---|---|---|---|
| 1,562,102 | 11/1925 | Massena . | |
| 1,840,021 | 1/1932 | Brooks . | |
| 5,026,360 | 6/1991 | Johnson et al. | 604/338 |
| 5,180,377 | 1/1993 | Holtermann | 604/342 |
| 5,322,522 | 6/1994 | Olsen | 604/342 |
| 5,322,523 | 6/1994 | Olsen | 604/342 |
| 5,364,379 | 11/1994 | Ozeene et al. | 604/342 |
| 5,647,861 | 7/1997 | Steer et al. | 604/338 |
| 5,662,628 | 9/1997 | Hollands | 604/342 |
| 5,662,629 | 9/1997 | Steer et al. | 604/338 |
| 5,693,036 | 12/1997 | Kilgour | 604/338 |

FOREIGN PATENT DOCUMENTS

| | | |
|---|---|---|
| 0 433 102 | 11/1989 | European Pat. Off. . |
| 0 381 393 | 8/1990 | European Pat. Off. . |
| 0 572 378 | 12/1993 | European Pat. Off. . |
| 2 259 342 | 3/1993 | United Kingdom . |
| 2 261 376 | 5/1993 | United Kingdom . |
| 2 289 221 | 11/1995 | United Kingdom . |
| WO91/01118 | 2/1991 | WIPO . |

Primary Examiner—Robert A. Clarke
Attorney, Agent, or Firm—Stuart E. Krieger

[57] ABSTRACT

An ostomy coupling has a first coupling member and a second coupling member. These are mutually interengageable and surround a region which includes a stomal orifice. A springy resilient ring encircles the two coupling members and has a handle member which can be manipulated to cause the ring to be deformed such that radially-inwardly extending tabs on the ring are shifted between respective first positions in which the ring is undeformed and the tabs lock the two coupling members together and respective second positions in which the ring is deformed in such a way as to shift the tabs radially outwardly to positions where they permit separation of the two coupling parts. The ring has a portion which joins the ends of two limbs of the ring, said portion being readily deformable and optionally sufficiently elastic such that the limb ends are pulled towards each other by the elasticity of said portion.

9 Claims, 7 Drawing Sheets

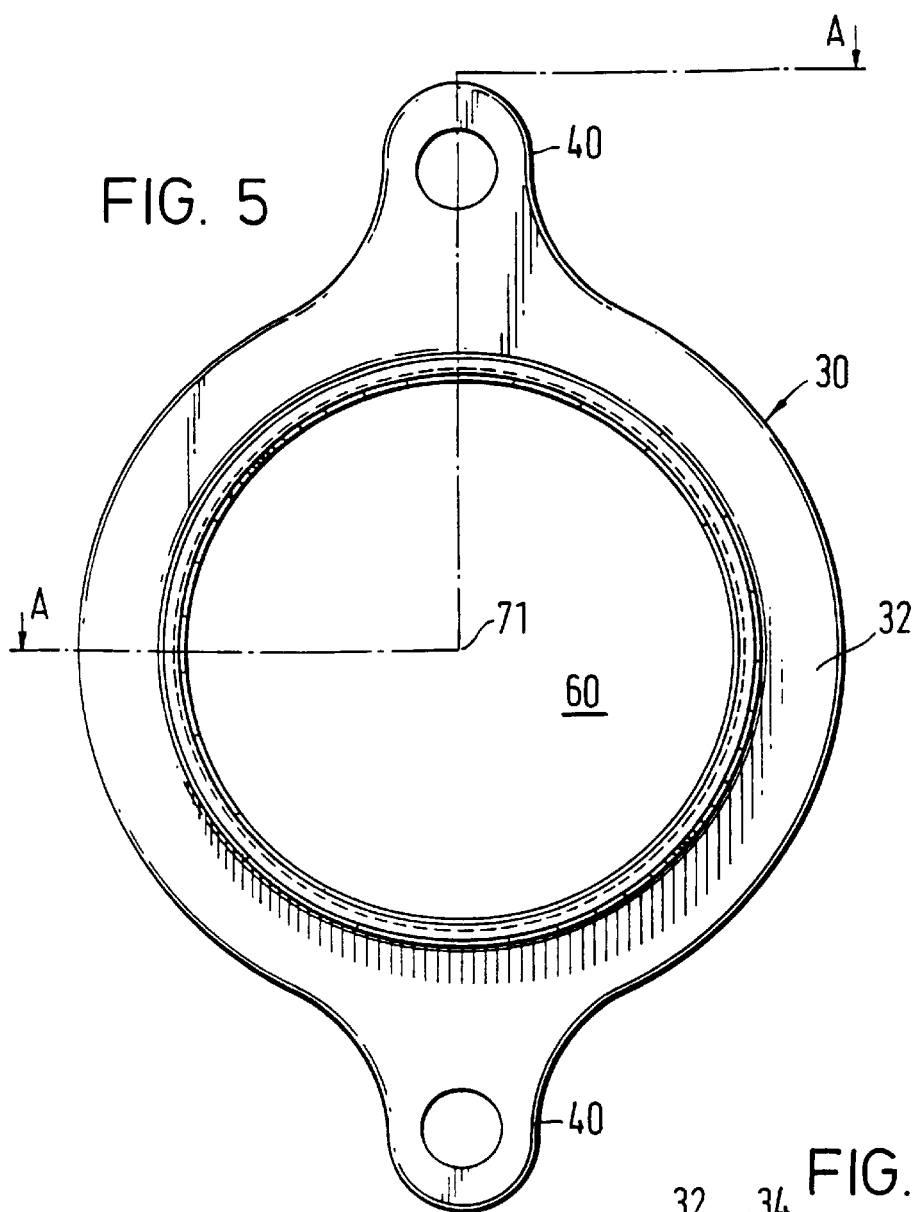
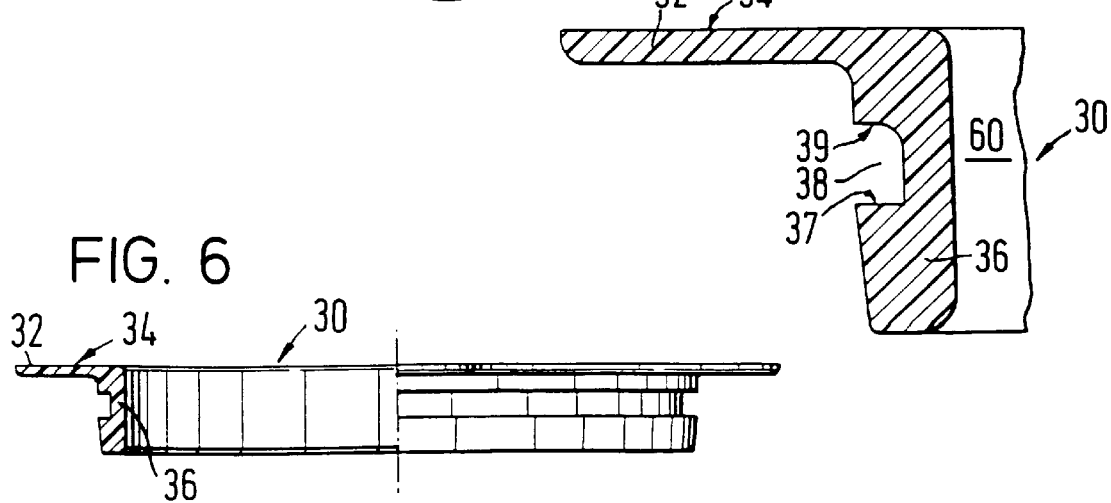

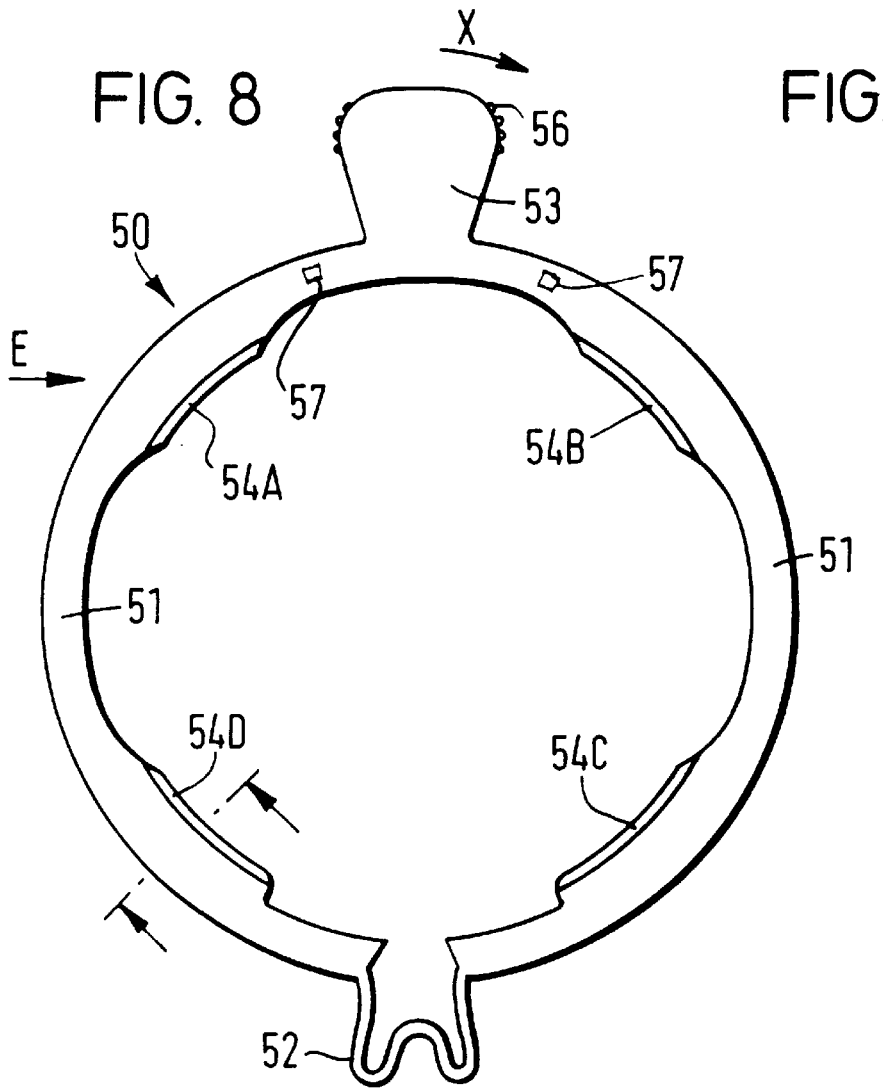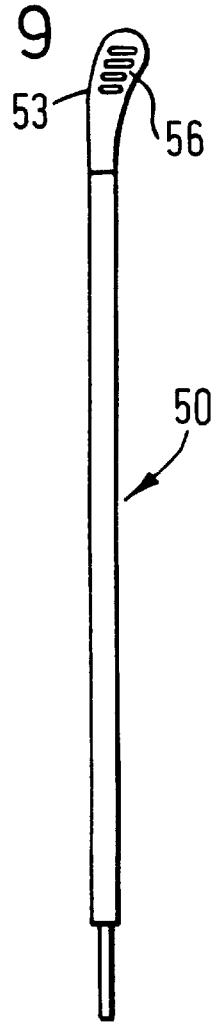

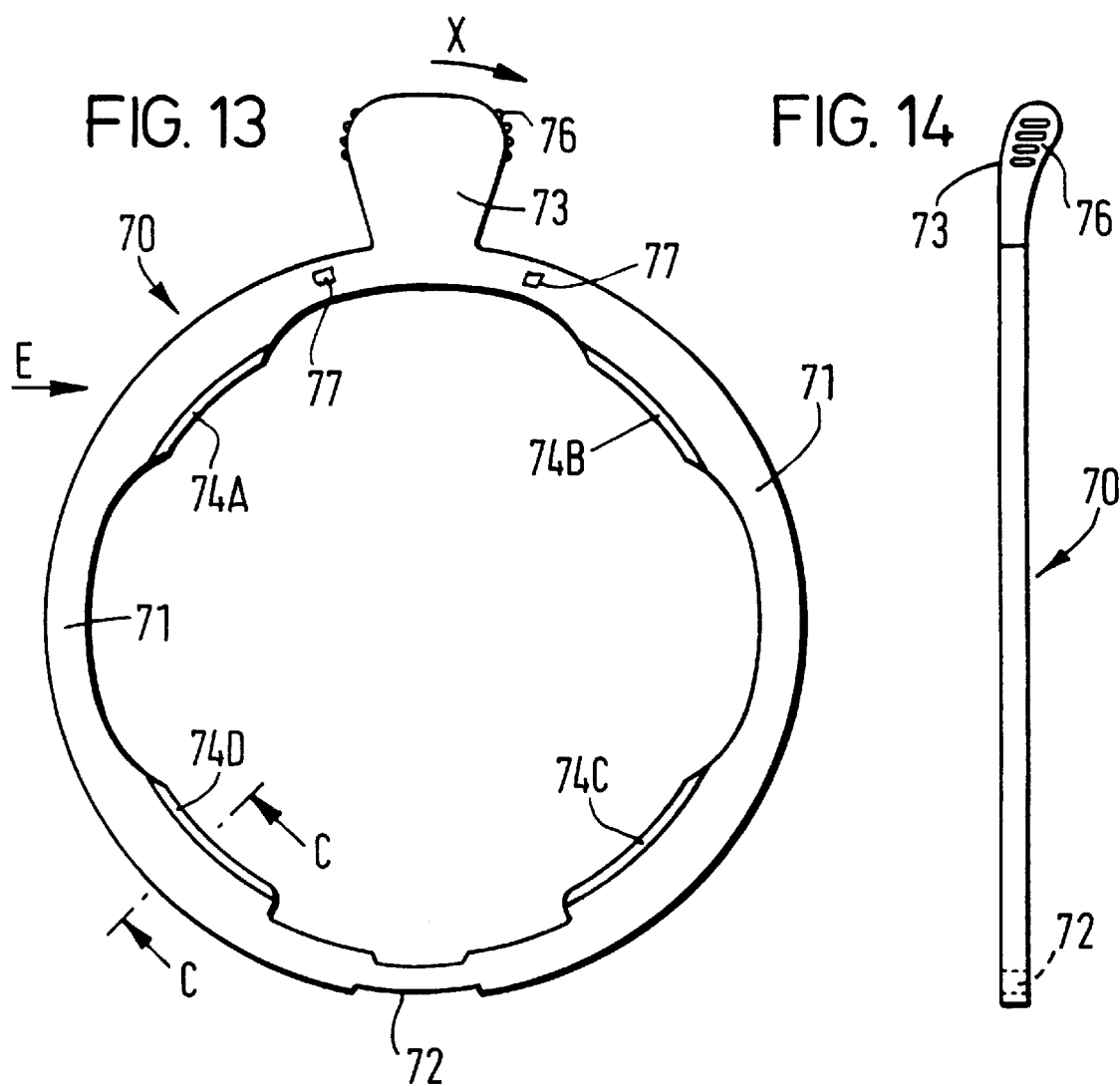

OSTOMY COUPLING

BACKGROUND OF THE INVENTION

This invention relates to an ostomy coupling.

The term "ostomy" is intended to include colostomy, ileostomy, urostomy and other surgical diversion procedures.

Ostomy couplings are used to connect and disconnect a bag for receiving a stomal discharge to and from a medical grade adhesive pad which is applied to the peristomal area of the skin of the wearer. Many designs of ostomy coupling are known. One which has enjoyed considerable world-wide commercial success is described and claimed in U.K. Patent No. 1,571,657.

An ostomy coupling in which locking and unlocking is achieved by deforming a ring is disclosed in our U.K. Patent Application No. 2,289,221A published on 15 Nov. 1995.

An ostomy appliance in which a V-section ring (see U.S. Pat. No. 5,322,522) holds coupling members together is disclosed in U.S. Pat. No. 5,322,523 and in European Patent 572 378B. Features of the design of U.S. Pat. No. 5,322,523 are that inwardly sprung tongues on the ring peripherally surround the joined coupling parts and that a press-button engagement device as well as a hook and detent engagement device are included, apparently in a quest for secure location of the locking ring on the coupling parts. It appears inevitable that quite intricate manipulation of this design of coupling is needed when applying or removing the bag.

It has been proposed by Kubo, in Japanese Utility Model No. 62-11610, published February 1985, that an ostomy device should have a double female ring structure which can interengage with a male ring. The male ring may be on the bag and the female ring on a skin-attachable adhesive pad, or vice-versa. An outer ring on the female coupling is circular and flexible and has a pair of inwardly-extending catches at opposite ends of a diameter. By pressing on two diametrically extending lugs, whose diameter is substantially at right angles to the diameter joining the catches, the outer female ring is deformed so that the catches are caused to move radially outwardly, so permitting separation of the two coupling parts. This arrangement, though perhaps operable in theory, has serious disadvantages in practice. To the best of the present Applicant's knowledge and belief it has not come into medical use anywhere in the world. A further disadvantage of Kubo and of many present day ostomy couplings is that they extend outwardly from the body an undesirable distance, and so cause bulges or bumps under the wearer's clothing.

An ostomy coupling designed by the present Inventor is described in U.K. Patent Application No. 95 07520.5. This comprises two coupling parts and a springy split ring carrying locking tabs. These tabs can enter holes in one of the coupling parts to hold the parts together, and can be withdrawn by rotating the ring to allow the parts to be separated.

SUMMARY OF THE INVENTION

According to one aspect of the present invention, an improved design is provided, in which a first coupling member and a second coupling member are mutually interengageable and surround a region which includes a stomal orifice, the coupling also including a springy resilient ring which encircles the two coupling members and has a handle member which can be manipulated to cause the ring to be deformed such that radially-inwardly extending tabs on the ring are shifted between respective first positions in which the ring is undeformed and the tabs lock the two coupling members together and respective second positions in which the ring is deformed in such a way as to shift the tabs radially outwardly to positions where they permit separation of the two coupling parts, the ring also comprising a portion which joins the ends of two limbs of the ring, said portion being readily deformable and optionally sufficiently elastic such that the limb ends are pulled towards each other by the elasticity of said portion.

According to another aspect of the present invention, an ostomy coupling is provided, in which a first coupling member and a second coupling member are mutually interengageable and surround a region which includes a stomal orifice, the coupling also including a springy resilient ring which encircles the two coupling members and has a handle member which can be manipulated to cause the ring to be deformed such that radially-inwardly extending tabs on the ring are shifted between respective first positions in which the ring is undeformed and the tabs lock the two coupling members together and respective second positions in which the ring is deformed in such a way as to shift the tabs radially outwardly to positions where they permit separation of the two coupling parts, the ring also comprising a means for joining the ends of two limbs of the ring, said means for joining being capable of applying a force to pull the limb ends towards each other.

According to a further aspect of the invention, there is provided a locking ring for use in an ostomy coupling, the ring comprising two springy limbs and a joining portion. In one embodiment the joining portion is a stretchable elastic thermoplastics material and in another embodiment the joining portion is a sinuous springy resilient thread-like element.

According to a preferred embodiment of the invention, the limbs of the ring are made of a relatively rigid but springy plastics material, for example an acetal resin, and the tabs carried by it are provided with curved or angled ramp surfaces which, when the ring is deformed by a force tending to rotate it relative to the coupling members, causes the tabs to be withdrawn from slots so permitting the two coupling members to be separated.

In an advantageous embodiment of the invention, two springy limbs of the endless ring each carry a pair of inwardly projecting tabs, the ring is rotatable relative to one of the coupling members, and rotary movement of the ring may be limited by suitably-positioned arcuately-spaced studs on the first coupling member.

A valuable feature of the invention is that the ring is reliably maintained on the first coupling member even when the second coupling member is removed therefrom. Additionally, when the first and second coupling members are coupled together, the handle on the ring is accessible at an upper region of the coupling, and can be shifted between its two limit positions. In one of these the coupling is locked and in the other, unlocked. The manipulation needed to shift the ring in a rotary direction is simple and straightforward, and can be readily achieved even by the elderly or infirm. The ring because of its springy nature immediately springs back to its "handle top dead centre" position once the wearer of the coupling releases the handle.

In one preferred embodiment of the invention, the endless ring has two limbs which together extend around about 350° and a thread of resilient plastics material joining the ends of these limbs. This thread material is sufficiently strongly resilient that it exerts a force on the ends of the limbs sufficient to prevent them moving apart in their normal rest position. In that position, the coupling is held closed by engagement of tabs in holes. This force can be overcome by rotating the ring relative to the body side coupling member.

In a second preferred embodiment of the invention, the endless ring has two limbs which are joined by a short length of elastic plastics material. This material likewise exerts a force tending to hold the ring closed, although of course this force can be overcome by a manual rotational shifting of the ring, achieved by a movement of the handle as indicated by arrow X of FIG. 8 or 13.

In another embodiment of the invention, the means for joining the ends of two limbs of the ring may consist of a commonplace elastic band, each of the opposed ends of the respective limbs then being provided with a suitable hook so that the elastic band can be temporarily attached between the limb ends. Other suitable joining arrangements may occur to one skilled in the art.

The invention will be better understood from the following description of an illustrative example thereof, given with reference to the accompanying drawings in which:

BRIEF DESCRIPTION OF THE DRAWINGS

FIG. 5 is a top view of a second coupling member in accordance with the present invention;

FIG. 6 is a side view of the second coupling member shown in FIG. 5 in partial section;

FIG. 7 is a sectional view of a portion of the second coupling member shown in FIG. 5;

FIG. 8 is a top view of a locking ring in accordance with the present invention;

FIG. 9 is a side view of the locking ring of FIG. 8 taken in the direction of the arrow E of FIG. 8;

FIG. 13 is a top view of a second embodiment of a locking ring;

FIG. 14 is a side view of the locking ring of FIG. 13 taken in the direction of the arrow E of FIG. 8;

DETAILED DESCRIPTION OF THE DRAWINGS

The present invention has been developed with a view to meeting the need for an ostomy coupling which can be easily manipulated by old or infirm and sometimes confused persons to separate a bag side coupling from a body side coupling member which is attached to a medical grade adhesive pad. As well as permitting easy manipulation, the invention aims to substantially avoid pressure on the tender peristomal area and to provide clear and unmistakable indications when the coupling members are (a) unlocked and ready for separation, and (b) locked together. This is a feature of importance to ostomates, who need to feel confident that no leakage will occur, and that inadvertent detachment is virtually impossible.

Another valuable feature of the invention is that, upon the wearer releasing the handle, the ring springs back to its rest position, which may be "top dead centre" but could be a different position. This "automatic" return of the lock ring to its normal position is believed to be most useful in practice and to be novel in ostomy couplings. The wearer does not need to touch the handle when fitting a bag-side coupling to the body side coupling in place on the body; but to remove it the handle is rotated either way to an "unlock" position. Hence one can only get the bag off when the handle is held in the "unlock" positions and once the bag is off the lock automatically springs back when released, thereby ensuring automatic locking upon the fitting of the next bag.

A preferred embodiment of a coupling according to the present invention comprises three parts, a first coupling member 10, FIGS. 1–4; a second coupling member 30, FIGS. 5 to 7; and three alternative versions 50, 70, 80 of a locking ring, FIGS. 8 and 9, FIGS. 13 and 14, and FIGS. 15 and 16.

Figure 10:
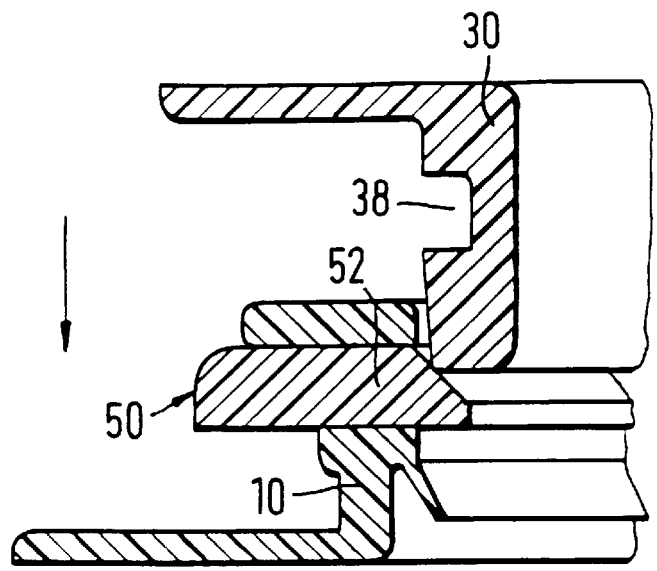
FIG. 10 is a cross-sectional view showing a second coupling in position for downward movement onto a first coupling and locking ring.
Figure 11:
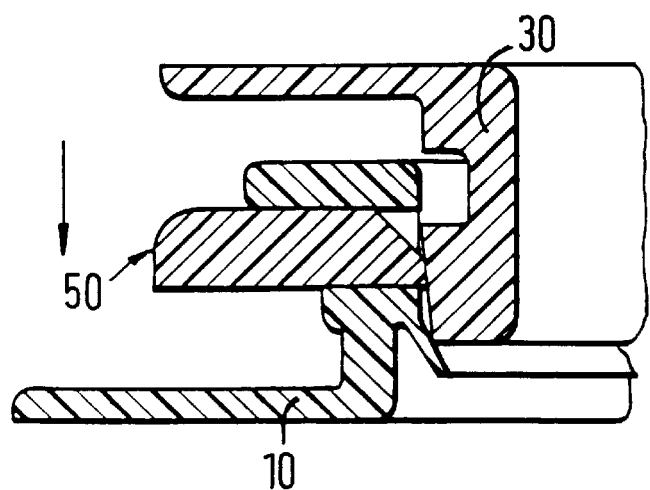
FIG. 11 is a cross-sectional view showing a second coupling partly pushed downward onto a first coupling and locking ring.
Figure 12:
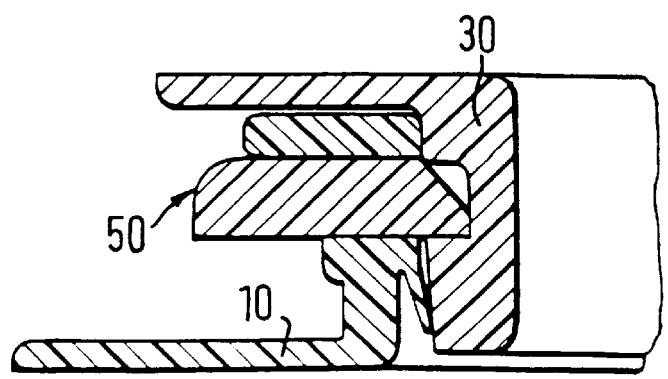
FIG. 12 is a cross-sectional view showing a second coupling coupled to a first coupling and locked together with a locking ring.

Referring firstly to FIGS. 10 to 12, the bag side coupling member 30 in use is presented to and engaged with the body side coupling member 10 which is attached to the peristomal area in the normal way. The member 30 is pushed into the body side member 10 as shown by the arrow. FIG. 9 shows an intermediate stage in the coupling operation; the ring 50 has been deformed so that a limb thereof is shifted radially outwardly as the part 30 slides past the chamfer on the tab 52 of the ring 50. FIG. 10 shows the completion of the action; ring 50 springs back into the recess 38 in the part 30 and holds the two coupling members locked together. Uncoupling is effected by a rotational movement of the ring 50 achieved by pushing the handle portion of the ring to rotate the ring, as will be explained in more detail later in this specification.

Referring now to FIGS. 1–4, the first coupling member 10 will usually be the body side coupling member, and the second, the bag side member. However, without departing from the invention, the first coupling member could be the bag side member and the second coupling member could be the body side member, although this arrangement is currently less preferred.

The body side coupling member 10 may be an injection moulding made of high or low density polyethylene, or EVA, and comprises a flange 12 having a surface 14 which in practice is attached in any suitable way such as by adhesive or by heat or RF or ultrasonic welding to a pad of medical grade adhesive. The purpose of such a medical grade adhesive pad is to attach the ostomy appliance to the skin of the wearer. The pad comprises a base which is preferably a thin film of polymeric material such as polyethylene and an adhesive layer situated on the rear surface of a base. Such an adhesive layer is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents. Medical grade adhesive pads of other compositions may alternatively be used.

Figure 2:
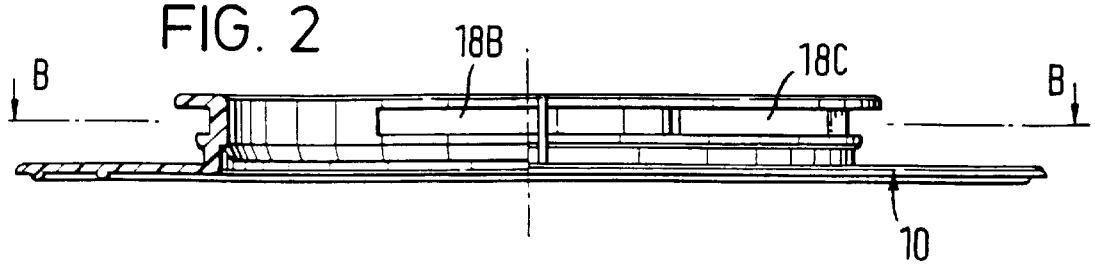
FIG. 2 is a side view of the first coupling member shown in FIG. 1 in partial section.

The body side coupling member 10 has a peripheral wall 16, which as seen in FIG. 2 is circular with apertures 18A, 18B and 18C therein. As shown, there are three apertures but in a presently-preferred design of body side coupling, there are four apertures, each receiving one of the four tabs illustrated in FIG. 8 or FIG. 13. The aperture 18A at the top of the coupling member (in normal position of wear) subtends about 65°, and each of the apertures 18B and 18C subtends about 50°. In one embodiment in which there are four apertures, they would be located at 90° centres, and each aperture would subtend about 30°, although apertures of other extent or other position could be used. While in a preferred embodiment of the invention and as illustrated the first and second coupling members are generally circular in form, the invention is not considered to be limited to this, and the coupling members instead could be oval or other closed-loop shape. For brevity of description, however, circular coupling members are referred to. The wall 16 is upstanding from the flange 12. A further flange 17 extends radially outwardly from the wall 16.

At the base of the wall 16, extending inwardly, is a continuous, optionally resilient, deflectable sealing strip 20 (FIG. 4) which extends around the stomal orifice 60. The chief function of this strip is to inhibit leakage but it also serves to accommodate tolerances if during moulding of the coupling members, some slight divergence from the designed dimensions should occur.

At the opposite end of a diameter from the aperture 18B, on the external surface of the wall 16, there is provided a stop which is formed by a pair of nibs or walls 22A,22B, which project outwardly from the wall 16 and are also integral with the flange 14. Of course a single rib could be used instead. The end of the wall 16 remote from the flange 12 may optionally have an external chamfer. As seen in FIG. 10, in the assembled condition of the coupling members, the wall 16 of the body side member 10 surrounds the bag side member 30.

Figure 1:
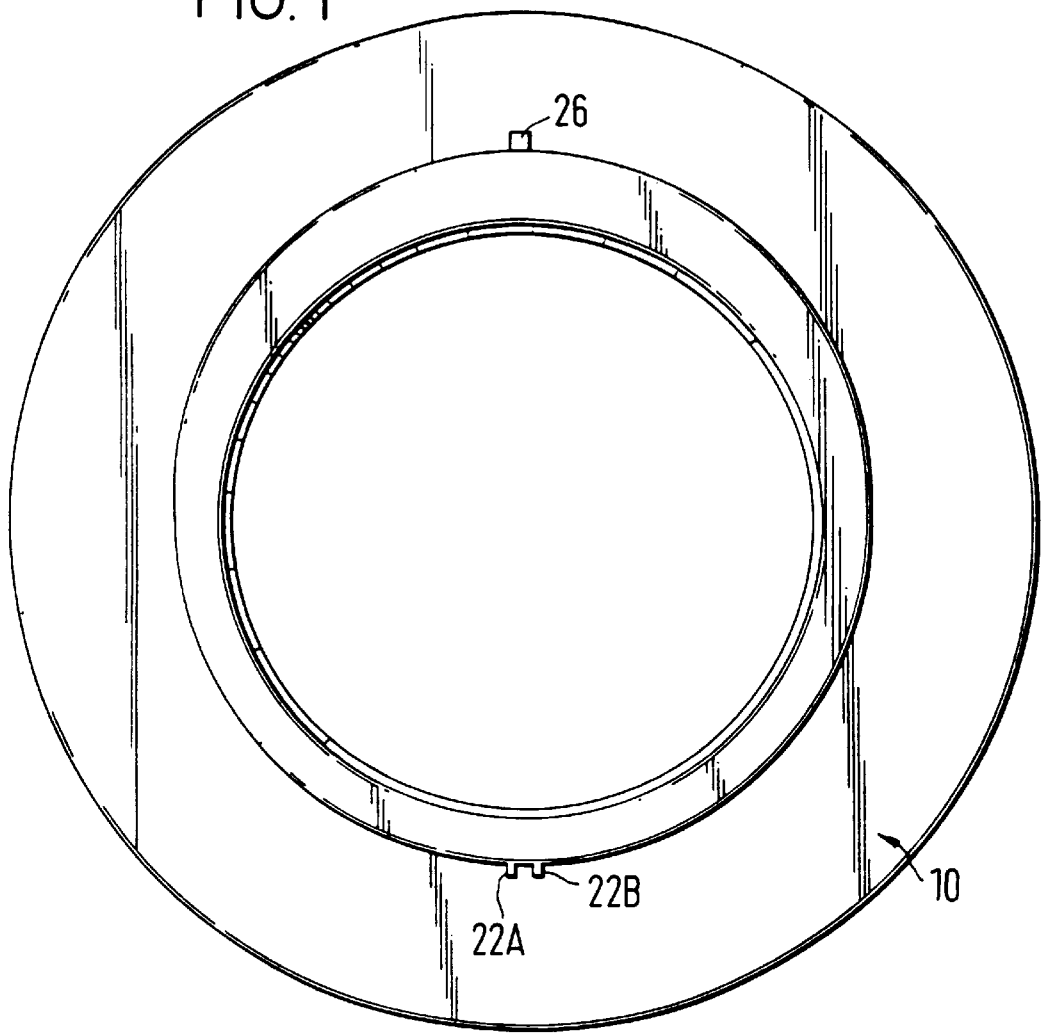
FIG. 1 is a top view of a first coupling member in accordance with the present invention.
Figure 3:
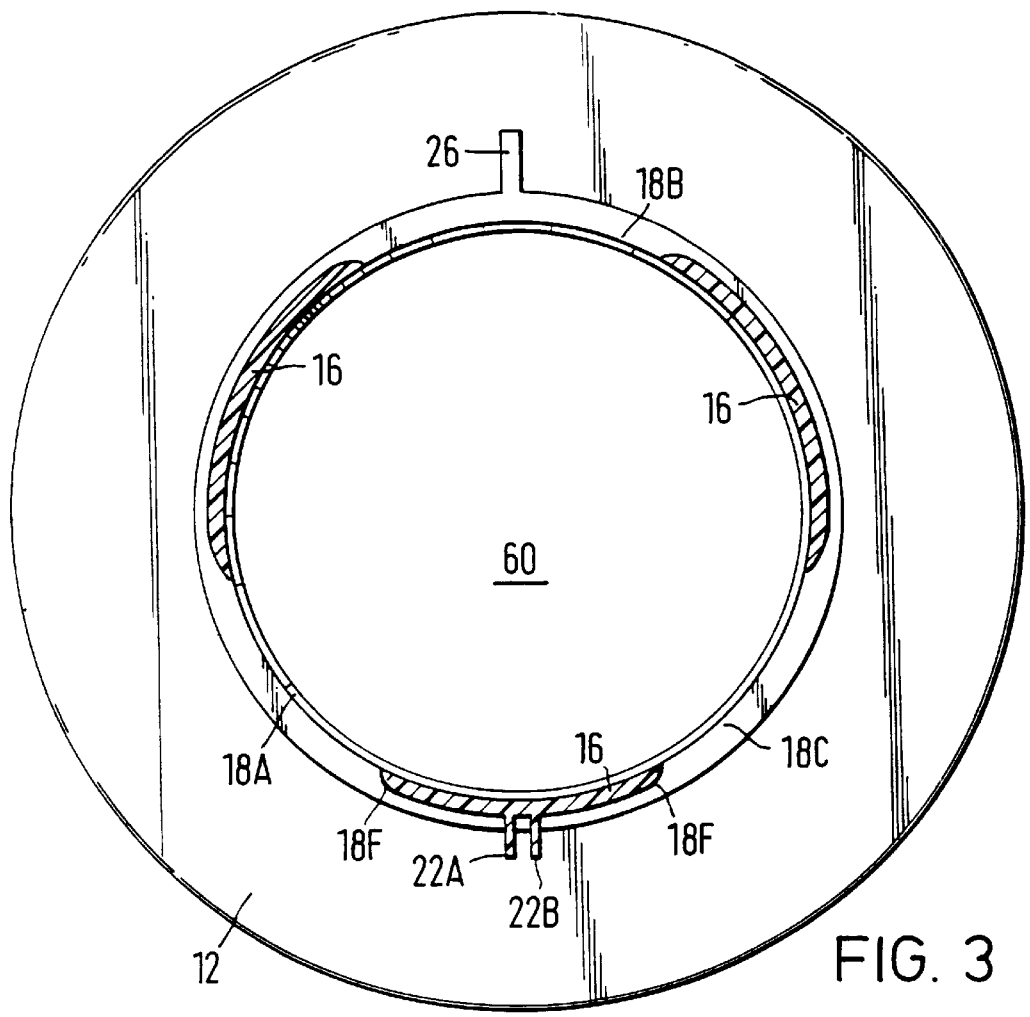
FIG. 3 is a sectional view taken along line B—B of FIG. 1.
Figure 4:
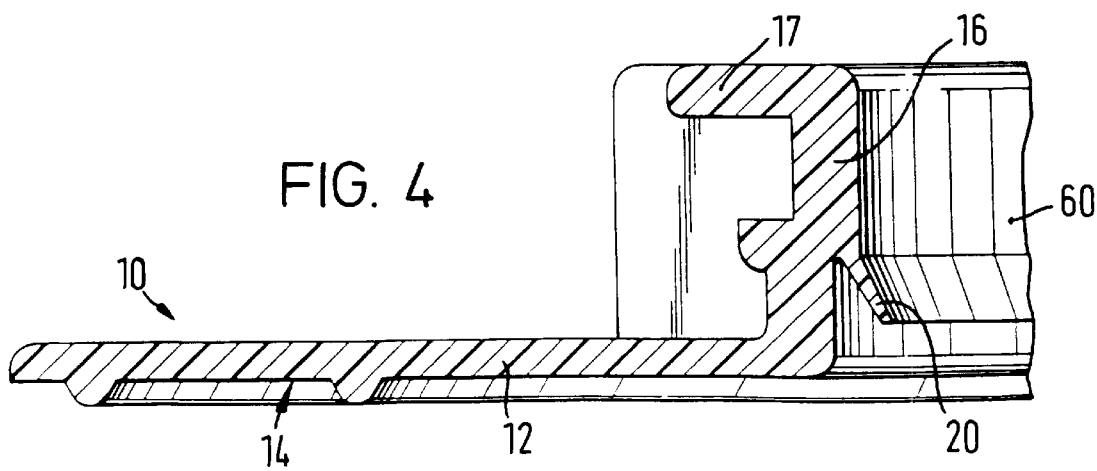
FIG. 4 is a side view of a portion of the first coupling member shown in FIG. 1.

A lug 26, FIG. 1 or 3, extends radially outwardly externally of the wall 16, and serves to limit the extent of arcuate motion of a handle portion 51 of a locking ring, as will be later described.

The flange 17 of the body side coupling member 10 is shaped so that its maximum width is at a region which is at the top of the coupling in the normal position of wear. Its width decreases as one moves around the coupling to the 90° and 270° locations; its width is uniform over substantially the bottom half of the coupling. The purpose of this widening of the flange is to more securely retain the ring on the body side coupling member.

Referring now to FIGS. 5, 6 and 7, these depict a bag side coupling member 30 which is of simple design. The bag side coupling member 30 may also be an injection moulding and may be of EVA. It comprises a flange 32, having a surface 34 to which an ostomy bag or pouch (not shown) is attached. Extending from the flange, at right angles thereto (although other angles would be possible) is a cylindrical wall 36 which, as indicated above, in use fits within the wall 16 of the first coupling member. A groove 38 in the radially external surface of the wall 36 extends completely around that wall and has a flat surface 37 remote from the flange 32 and a curved surface 39 nearer to the flange 32, these surfaces 37 and 39 bounding the channel or groove 38. Belt attachment tabs 40 and a pull tab (not shown) may optionally be included. However, the inventor's present view is that such tabs can be dispensed with since, in the unlocked condition, the two coupling members can be quite readily separated by simply grasping the flange 32 between finger and thumb and pulling the second coupling member directly (axially) away from the first coupling member 10. As will be appreciated, the first and second coupling members surround a stomal orifice 60, into which normally projects the stoma of the person who has undergone surgery.

Referring now to FIGS. 8 and 9, these depict one preferred embodiment of locking ring 50 for use in the present invention. This is a ring comprising two springy limbs 51 and a resilient springy joining portion and is of generally circular formation. The limbs 51 and the joining portion 52 made of a relatively rigid but springy plastics material such as an acetal resin. For example, good results have been achieved with an acetal copolymer known as "KEMATAL" (Regd. Trade Mark) which is also referred to as polyoxymethylene (POM) and is available from Hoechst. This is a crystalline thermoplastic with an exceptionally stable polymer structure; a suitable grade is "HOSTAFORM" (Regd. Trade Mark) C.27021.

The ring 50 is depicted in FIG. 8 in its normal or unstressed condition. It comprises a handle 53 and four inwardly projecting tabs, 54A, 54B, 54C and 54D. The tabs are located around the ring at about 90 degree spacing, as shown. The tabs 54 project inwardly from an inner surface of the ring 50 and are integral with it. The extent of inward projection is determined according to the radius of the ring. As will be appreciated, ostomy couplings are made in various sizes, ranging from about 32 millimetres to about 57 millimetres or more. The larger sizes would be used post-operatively, and would have tabs which are wider in the radial direction.

The tabs 54A and 54B are provided with smoothly-sloping end portions 54E. The tabs 54C and 54D have smoothly sloping surfaces 54F. The smooth shallow slope of the surfaces 54E and 54F assist in enabling the handle (and hence the ring 50) to be freely movable within limits in a rotational direction.

The handle 51 optionally has ribs 56 thereon (see FIGS. 8 and 13) to provide a rough surface which can be gripped. This makes shifting the ring an easier task for elderly or infirm users. To avoid the handle 51 catching in clothing, it is preferably canted inwards, towards the body side coupling member, by a few degrees, as seen in FIG. 9 or 14. The ring 50 carries a pair of stops 57, which limit the rotation of the ring in either rotary direction. One or other of the limit stops 57 comes into contact with the lug 26 (FIG. 1), when the ring 50 is rotated relative to the body side coupling 10.

When it is desired to unlock the coupling and thereby release the bag side member so that it may be axially drawn off the body side coupling member, the handle 51 is rotated a short distance, e.g. up to about 15°, in either rotary direction away from its central position.

As a result, the tabs 54 are shifted circumferentially in one or other rotary direction, and a surface of each tab rides up on the edge of the corresponding aperture 18 seen in FIG. 2. Thus, the tabs are forced in directions approximately radially outwardly, this being permitted by the springy nature of the material of the ring 50.

As a consequence of rotation of the handle, the tabs 54 as stated are forced generally radially outwardly and clear the groove 38 of the bag-side coupling. Also the sinuous joining portion 52 is somewhat straightened, while continuing to hold the ring on the bodyside coupling, due to its inherent resilience. With the ring shifted rotationally relative to the coupling part 10, it is readily seen that the tabs are withdrawn from the stomal orifice 60 and also withdrawn from the channel 38. The bag and bag side coupling member thereon can be removed from the body side coupling member by a gentle axial pull. Referring now to FIGS. 13 and 14, these show an alternative design of locking ring 70 which however has many resemblances to the locking ring 50. In FIGS. 13 and 14, like parts to those in FIGS. 8 and 9 are given corresponding reference numerals but in the 70s rather than the 50s. The significant difference between ring 50 and ring 70 is that the ring 70 is made of two limbs 71 of acetal resin (or like springy plastics) and a joining portion 72 of a plastics elastomer whose thickness is substantially equal to the thickness of the limbs 71 but whose width (radial extent) is slightly less than that of the limbs 71. The plastics elastomer chosen is such that it is stretchable to up to about 150 per cent of its length at rest. The joining portion 72 could alternatively be made of rubber or synthetic rubber.

Figure 15:
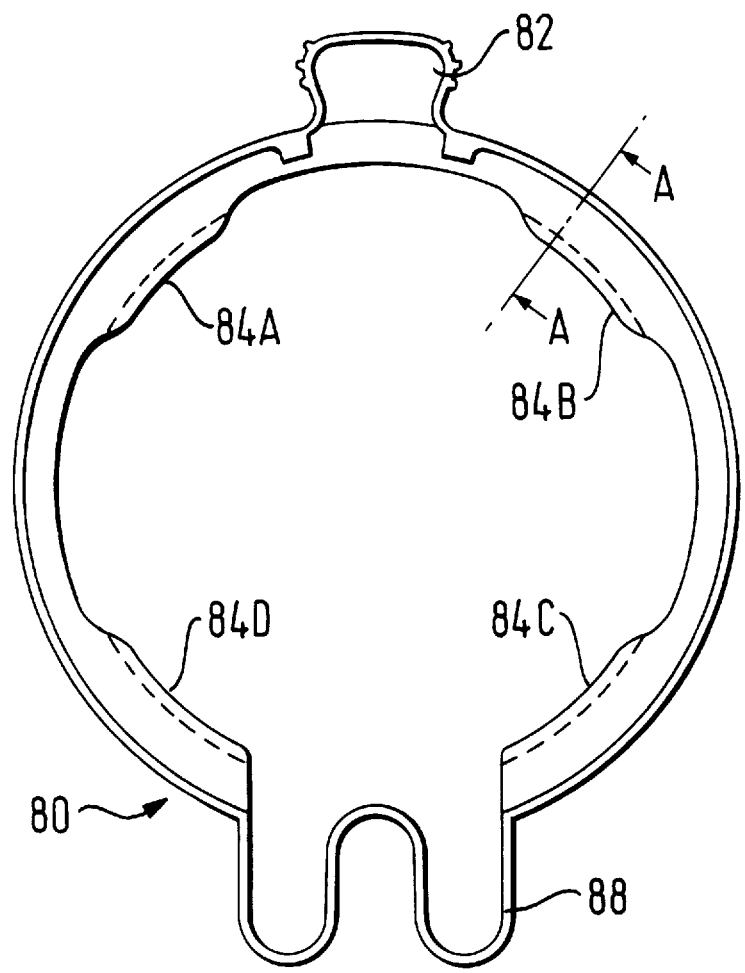
FIG. 15 is a top view of a third embodiment of a locking ring.
Figure 16:
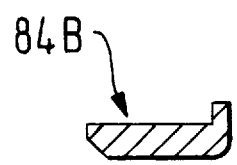
FIG. 16 is a sectional view taken along line A—A of FIG. 15.

FIGS. 15 and 16 illustrate a further alternative design of locking ring 80 which is mainly circular and has a handle 82, four tabs 84A, 84B, 84C and 84D, two stop members 86, and a springy joining portion 88 which is of sinuous shape, and may be of approximately one millimeter in thickness. The ring 80 is of a springy nature, and is preferably made of an acetal resin, for example that known as DELRIN 500-NC10 (acetal) available from Du Pont (UK) Limited, Hemel Hempstead, Hertfordshire. The handle 82 is provided with ribs to enable it to be more securely grasped with finger and thumb. As with the rings shown in FIGS. 8 and 13, the tabs have curved surfaces. One advantageous aspect of either of the joining portions 52 (FIG.8) or 88 (FIG. 15) is that their connection to the ends of the limbs of the ring 50 or 80 results in a force being applied to the ring ends tending to urge the tabs 54C and 54D (or the tabs 84C and 84D) inwardly in a generally radial direction. This assists in ensuring that these tabs remain securely engaged within the groove 38 (FIG.7) even if the spring resilience of the remainder of the ring has diminished somewhat due to use or ageing of the material of the ring. The elastic portion 72 or the "means for joining" referred to above serve a similar purpose. In use rotation of the ring causes the surfaces of the tabs to engage the edge of the relevant aperture and be moved generally radially outwardly so as to permit the coupling parts to be separated from one another. The tab shape can be seen from FIG. 16 which is a cross-section on the plane A—A of FIG. 15.

The present invention can be employed in a design of ostomy coupling which is has a body-side member which includes an annular channel. One such design is shown in European Patent Application No. 96302557.2. The present invention could be employed in this design simply by including a springy or elastic joining portion located between and joined to the ends 23, 24 of the split ring 20 shown in FIG. 3 of the said European Patent Application. Such a modification would increase the security provided by the ring 20.

It will be seen that the particular embodiments of the invention described herein provides couplings which can be easily disassembled and assembled by persons who are not nimble, which can be assembled and disassembled with only very light pressure being applied either during coupling or uncoupling to the tender peristomal area, and which can readily be made in any coupling size. The rings 50, 70 or 80 are in effect made captive within the coupling members 10 and 30, and so cannot escape; moreover, the positive rotational movement of the handle between two fixed positions gives assurance to the wearer such that he or she knows when the coupling is properly locked, because in the properly locked condition, the handle is at top dead centre. If desired, by choosing an appropriate springiness of the material for the locking ring, the ring can be made to automatically spring back towards top dead centre position when the wearer releases his/her grip of the handle. While a ring having four tabs is currently preferred, three or five or any other convenient number could be employed.

What is claimed is:

1. An ostomy coupling, comprising:
   a first coupling member and a second coupling member capable of being being detachably coupled together; and
   a locking ring including a loop of springy resilient material, said ring including tabs thereon and a handle portion extending therefrom for manipulating said ring into a first position in which said ring is undeformed and said tabs lock said coupling members together, and a second position in which said ring is deformed to permit said coupling members to separate, said locking ring having two limbs with an elastic portion extending therebetween.

2. The ostomy coupling as claimed in claim 1 wherein said elastic portion is deformable and arranged so that said limb ends are pulled towards each other by the elasticity of said portion.

3. The ostomy coupling as claimed in claim 1 wherein said elastic portion is capable of applying a force so that said limb ends are urged towards each other.

4. The ostomy coupling as claimed in claim 1 wherein said ring has limbs made of a relatively rigid, springy plastic material, said tabs are provided with curved or angled ramp surfaces, and said ring is deformable by a force tending to rotate it relative to said coupling members so that said tabs are withdrawn permitting said two coupling members to be separated.

5. The ostomy coupling as claimed in claim 1 wherein said ring carries inwardly projecting tabs, said ring being rotatable relative to one of said coupling members, and said first coupling member includes suitably-positioned, arcuately-spaced studs for limiting rotary movement of said ring.

6. The ostomy coupling as claimed in claim 1 wherein when the first and second coupling members are coupled together, said handle on said ring is accessible at an upper region of said coupled members, and shiftable between two limit positions, said coupling members being locked in one limit position and unlocked in said other limit position.

7. The ostomy coupling as claimed in claim 6 wherein said ring, at one limit position of rotation, has its handle at top center.

8. An ostomy coupling comprising first and second coupling parts and an endless rotable locking ring for locking said first and second coupling parts, said ring having two limbs which together extend substantially around said ring and a joining portion of a stretchable elastic thermoplastics material joining the ends of said two limbs, said locking ring being expandable at said joining portion to an expanded position upon rotation of said ring to permit coupling and uncoupling of said first and second coupling parts and contractable at said joining portion from said expandable position to a resting position for locking said first and second coupling parts together.

9. The ostomy coupling as claimed in claim 8 wherein said joining portion is sufficiently strongly resilient that it exerts a force on the ends of said limbs sufficient to prevent them moving apart in their normal rest position.

* * * * *